US011272978B2

United States Patent
Mori

(10) Patent No.: US 11,272,978 B2
(45) Date of Patent: Mar. 15, 2022

(54) ABLATION NEEDLE DEVICE, HIGH-FREQUENCY ABLATION TREATMENT SYSTEM, AND CHEMICAL ABLATION TREATMENT SYSTEM

(71) Applicant: Japan Lifeline Co., Ltd., Tokyo (JP)

(72) Inventor: Kenji Mori, Tokyo (JP)

(73) Assignee: Japan Lifeline Co., Ltd., Tokyo (JP)

( * ) Notice: Subject to any disclaimer, the term of this patent is extended or adjusted under 35 U.S.C. 154(b) by 714 days.

(21) Appl. No.: 16/018,839

(22) Filed: Jun. 26, 2018

(65) Prior Publication Data
US 2018/0296263 A1 Oct. 18, 2018

Related U.S. Application Data

(63) Continuation of application No. PCT/JP2016/087522, filed on Dec. 16, 2016.

(30) Foreign Application Priority Data

Jan. 20, 2016 (JP) .................. 2016-009262

(51) Int. Cl.
*A61B 18/14* (2006.01)
*A61B 18/06* (2006.01)
(Continued)

(52) U.S. Cl.
CPC .......... *A61B 18/1477* (2013.01); *A61B 18/06* (2013.01); *A61B 2017/00477* (2013.01); *A61B 2018/00005* (2013.01); *A61B 2018/00511* (2013.01); *A61B 2018/00577* (2013.01); *A61B 2018/00821* (2013.01);
(Continued)

(58) Field of Classification Search
CPC combination set(s) only.
See application file for complete search history.

(56) References Cited

U.S. PATENT DOCUMENTS 5,334,145 A * 8/1994 Lundquist ......... A61M 25/0138
604/95.04
5,472,441 A * 12/1995 Edwards ................ A61N 5/045
606/41
(Continued)

FOREIGN PATENT DOCUMENTS

| CN | 102228392 | 11/2011 |
| JP | 2005-205002 | 8/2005 |
| JP | 2008-119523 | 2/2008 |

*Primary Examiner* — Michael F Peffley
*Assistant Examiner* — Amanda L Zink
(74) *Attorney, Agent, or Firm* — Muramatsu & Associates

(57) ABSTRACT

An ablation needle device is a needle device intended for an ablation treatment of an adrenal tumor with transvenous introduction of an injection needle into an adrenal gland. The ablation needle device includes a metal injection needle including a pointed tubular distal portion and a tubular proximal portion, and a grip portion attached to a proximal side of the injection needle. The proximal portion of the injection needle is given flexibility by forming a helical slit in a distal region of the proximal portion. An outer surface of the proximal portion is coated with resin. A distal end of the distal portion of the injection needle is closed. A plurality of fine holes are formed in an outer surface of the distal portion including the closed part. The grip portion has a liquid-injection port for supplying liquid into the lumen of the injection needle.

5 Claims, 10 Drawing Sheets

(51) Int. Cl.
*A61B 18/00* (2006.01)
*A61B 17/00* (2006.01)

(52) U.S. Cl.
CPC .............. *A61B 2018/00994* (2013.01); *A61B 2018/068* (2013.01); *A61B 2218/002* (2013.01)

(56) References Cited

U.S. PATENT DOCUMENTS

| | | | |
|---|---|---|---|
| 5,531,719 A * | 7/1996 | Takahashi | A61M 25/0045 604/525 |
| 5,588,432 A * | 12/1996 | Crowley | A61B 8/4461 600/439 |
| 6,071,279 A | 6/2000 | Whayne | |
| 6,102,907 A * | 8/2000 | Smethers | A61B 18/1477 606/40 |
| 6,622,731 B2 * | 9/2003 | Daniel | A61B 18/1477 128/898 |
| 6,641,564 B1 * | 11/2003 | Kraus | A61B 17/3415 604/110 |
| 9,125,671 B2 * | 9/2015 | Germain | A61B 17/1642 |
| 9,724,107 B2 * | 8/2017 | Pellegrino | A61B 18/1487 |
| 10,463,380 B2 * | 11/2019 | Purdy | A61B 17/1631 |
| 10,568,611 B2 * | 2/2020 | Snow | A61B 10/0266 |
| 2002/0038129 A1 * | 3/2002 | Peters | A61B 17/32002 606/167 |
| 2004/0006336 A1 | 1/2004 | Swanson | |
| 2007/0162101 A1 * | 7/2007 | Burgermeister | A61M 25/0105 623/1.11 |
| 2008/0200972 A1 * | 8/2008 | Rittman | A61B 18/1492 607/117 |
| 2009/0247878 A1 | 10/2009 | Tanioka et al. | |
| 2009/0275966 A1 * | 11/2009 | Mitusina | A61B 17/32002 606/171 |
| 2011/0054487 A1 * | 3/2011 | Farnan | A61B 17/3478 606/108 |
| 2013/0035537 A1 | 2/2013 | Wallace | |
| 2014/0276713 A1 * | 9/2014 | Hoey | A61B 18/04 606/27 |
| 2017/0049514 A1 * | 2/2017 | Cosman | A61M 25/0662 |

\* cited by examiner

ABLATION NEEDLE DEVICE, HIGH-FREQUENCY ABLATION TREATMENT SYSTEM, AND CHEMICAL ABLATION TREATMENT SYSTEM

This is a continuation of International Application No. PCT/JP2016/087522 filed Dec. 16, 2016 which claims the benefit of priority of Japanese Patent Application No. 2016-009262, filed Jan. 20, 2016, the entire contents of which are incorporated herein by reference.

TECHNICAL FIELD

The present invention relates to an ablation needle device intended for an ablation treatment of an adrenal tumor with transvenous introduction of an injection needle into an adrenal gland, and also relates to a high-frequency ablation treatment system and a chemical ablation treatment system each including such an ablation needle device.

BACKGROUND ART

Primary aldosteronism is a hypertensive disease that appears when an adenoma (a tumor) that causes oversecretion of aldosterone, which is a vasopressor hormone, occurs in an adrenal gland.

In a treatment for primary aldosteronism, if there is oversecretion of aldosterone in one of the adrenal glands, the adrenal gland having the tumor is removed.

In contrast, if there is oversecretion of aldosterone in both of the adrenal glands, the patient needs to keep taking an antihypertensive drug because it is not allowed to remove both of the adrenal glands.

Recently, a treatment method for primary aldosteronism that causes oversecretion of aldosterone has been introduced, in which blood is sampled from an adrenal vein (adrenal venous sampling) with a catheter, which of the adrenal glands has abnormality is identified, the abnormal adrenal gland is accurately located through X-ray imaging or the like, a bipolar RF (radio-frequency) needle is inserted into the patient from his/her back, and the tumor is ablated.

CITATION LIST

Non Patent Literature

NPL 1: The Chemical Daily, Sep. 25, 2013

SUMMARY OF INVENTION

Technical Problem

In the above treatment method, the degree of invasion is lower than in the case of surgical removal of an adrenal gland, but the burden imposed on the patient is still heavy.

Furthermore, since the left adrenal gland is close to the pancreas and the intestinal tract, sticking a bipolar RF needle into a tumor in the left adrenal gland from the back is an anatomically difficult technique.

Such problems may be solved by an ablation treatment in which an ablation needle such as an RF needle is transvenously introduced into the adrenal gland.

However, a publicly known RF needle is highly rigid and less flexible and is incapable of following the complicated shapes of blood vessels. Therefore, such an RF needle may be stuck into a guiding catheter or a vascular wall before reaching the adrenal gland.

Moreover, if any biological tissue (adrenal tumor tissue) or thrombi adhere to the surface of the RF needle (an electrode) during ablation, the ablation treatment may become unable to continue.

Therefore, it is practically impossible to perform ablation treatment by transvenously introducing a publicly known RF needle into an adrenal gland.

The present invention has been conceived in view of the above circumstances.

An object of the present invention is to provide an ablation needle device that can be used for a transvenous ablation treatment, which is a novel treatment method for primary aldosteronism.

Another object of the present invention is to provide an ablation treatment system that can be used for the transvenous ablation treatment for primary aldosteronism.

Solution to Problem (1) An ablation needle device according to the present invention is an ablation needle device intended for an ablation treatment of an adrenal tumor with transvenous introduction of an injection needle into an adrenal gland, the ablation needle device comprising:

a metal injection needle including a pointed tubular distal portion and a tubular proximal portion whose lumen communicates with a lumen of the distal portion and has substantially the same diameter as the lumen of the distal portion; and a grip portion attached to a proximal side of the injection needle, wherein the proximal portion of the injection needle is given flexibility (bendability) by forming a helical slit at least in a distal region of the proximal portion, and an outer surface of the proximal portion is coated with resin, wherein a distal end of the distal portion of the injection needle (a distal-end opening of a typical injection needle) is closed, and a plurality of fine holes communicating with the lumen of the distal portion are formed in an outer surface of the distal portion including the closed part, and wherein the grip portion has a liquid-injection port for supplying liquid into the lumen of the injection needle (the lumen of the proximal portion and the lumen of the distal portion).

In such an ablation needle device, the rigidity of the distal region of the proximal portion of the injection needle is reduced to some extent by forming the helical slit therein. Therefore, the injection needle can be made flexible. Hence, the injection needle can be made to follow the shape of a blood vessel reaching the adrenal gland, and the distal portion of the injection needle can be made to reach a tumor site in the adrenal gland, without damaging the vascular wall.

Furthermore, since the plurality of fine holes communicating with the lumen are formed in the outer surface of the distal portion of the injection needle, a region around the distal portion can be irrigated with the ejection of the liquid, supplied into the lumen of the injection needle, from the plurality of fine holes.

(2) In the ablation needle device according to the present invention, it is preferable that a pitch of the slit formed in the proximal portion of the injection needle be continuously or intermittently reduced in a direction toward the distal end.

In such an ablation needle device, the rigidity of the proximal portion of the injection needle can be continuously or intermittently reduced in the direction toward the distal end. Accordingly, the needle device can exhibit especially high operability in the introduction of the injection needle into the adrenal gland.

(3) In the ablation needle device according to the present invention, it is preferable that the distal portion of the injection needle have a length of 1 to 6 mm, the region of the proximal portion of the injection needle where the slit is formed have a length of 40 to 700 mm, the injection needle have an inside diameter of 0.25 to 2.8 mm, and the fine holes each have a diameter of 0.01 to 0.25 mm.

(4) It is preferable that the ablation needle device according to the present invention be an ablation needle device intended for a high-frequency ablation treatment in which adrenal tumor tissue around the distal portion of the injection needle is heated by supplying a high-frequency current to the distal portion, the grip portion have an energization connector for supplying the high-frequency current to the distal portion of the injection needle, the injection port be an injection port for a physiological saline solution, and irrigation with the physiological saline solution through the plurality of fine holes be performed by injecting the physiological saline solution into the lumen of the injection needle from the injection port.

When such an ablation needle device is included in a high-frequency ablation treatment system to be described below, a high-frequency ablation treatment of an adrenal tumor (a transvenous ablation treatment for primary aldosteronism) can be performed assuredly. Furthermore, during the high-frequency ablation treatment, irrigation can be performed with the physiological saline solution through the plurality of fine holes formed in the distal portion of the injection needle. Hence, biological tissue or thrombi can be prevented from adhering to the surface of the distal portion of the injection needle.

(5) In the ablation needle device according to (4) described above, it is preferable that the grip portion have a thermocouple connector for measuring a temperature of the distal portion of the injection needle.

(6) In the ablation needle device according to the present invention, it is preferable that the injection port be an injection port for ethanol, and a chemical ablation treatment of an adrenal tumor is performed by injecting the ethanol into the lumen of the injection needle from the injection port and ejecting the ethanol from the plurality of fine holes.

When such an ablation needle device is included in a chemical ablation treatment system to be described below, a chemical ablation treatment of an adrenal tumor (a transvenous ablation treatment for primary aldosteronism) can be performed assuredly.

(7) A high-frequency ablation treatment system for an adrenal tumor according to the present invention comprises the ablation needle device according to (4);

a high-frequency power supply device connected to the energization connector;

a counter-electrode plate connected to the high-frequency power supply device;

physiological-saline-solution-supplying means connected to the injection port; and a guiding catheter for guiding the distal portion of the injection needle to the adrenal gland.

(8) A chemical ablation treatment system for an adrenal tumor according to the present invention comprises:

the ablation needle device according to (6);
ethanol-supplying means connected to the injection port; and a guiding catheter for guiding the distal portion of the injection needle to the adrenal gland.

Advantageous Effects of Invention

With the ablation needle device according to the present invention, the transvenous ablation treatment, which is a novel treatment method for primary aldosteronism, can be performed assuredly.

The ablation needle device according to the present invention is applicable to both a high-frequency ablation treatment and a chemical ablation treatment.

With the high-frequency ablation treatment system according to the present invention, the high-frequency ablation treatment (a transvenous ablation treatment) of an adrenal tumor can be performed assuredly.

With the chemical ablation treatment system according to the present invention, the chemical ablation treatment (a transvenous ablation treatment) of an adrenal tumor can be performed assuredly.

DESCRIPTION OF EMBODIMENTS

First Embodiment

Figure 1:
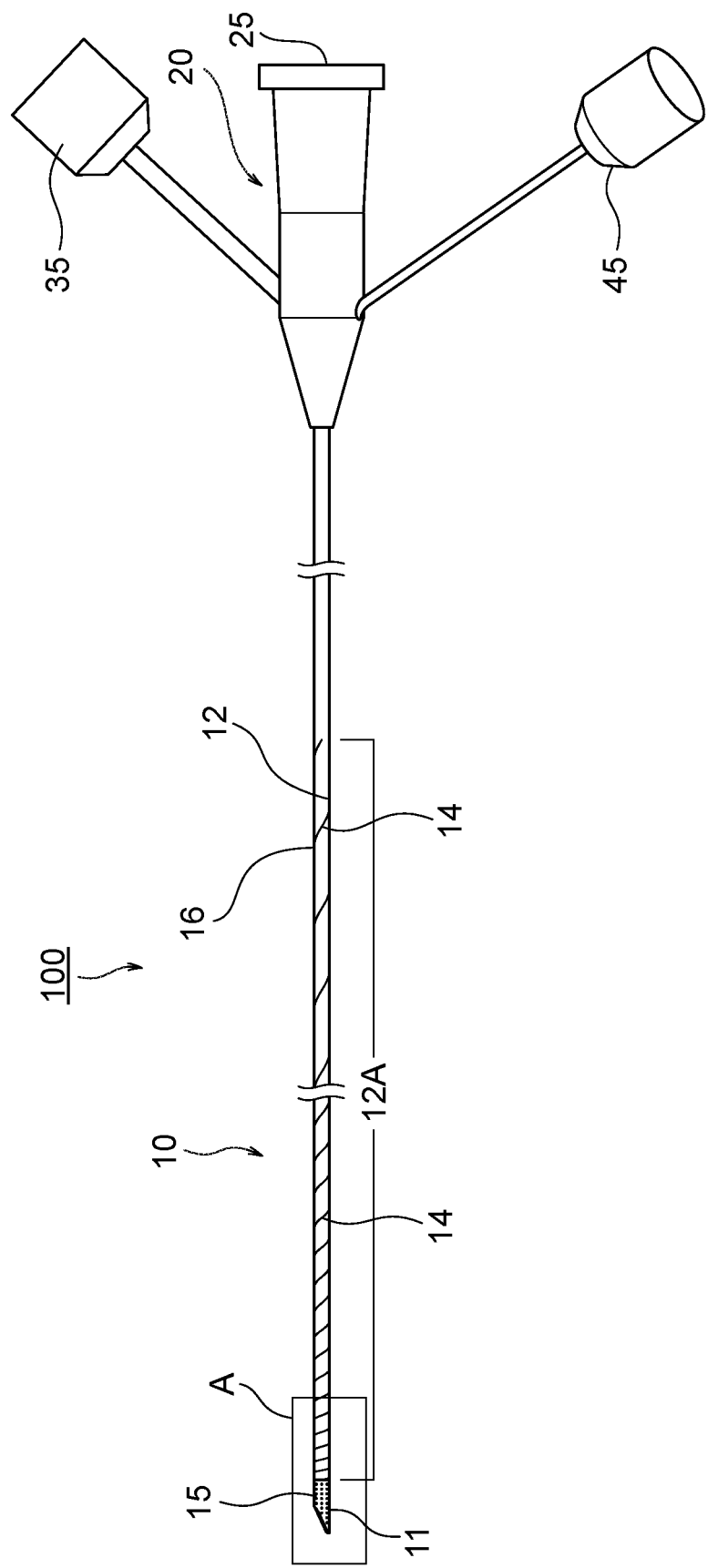
FIG. 1 is a side view of an ablation needle device according to an embodiment of the present invention.

An ablation needle device 100 according to the present embodiment is an ablation needle device intended for a high-frequency ablation treatment in which adrenal tumor tissue around a distal portion of an injection needle is heated by supplying a high-frequency current to the distal portion.

The ablation needle device 100 according to the present embodiment illustrated in FIGS. 1 to 5A and 5B is an ablation needle device intended for a high-frequency ablation treatment of an adrenal tumor with transvenous introduction of an injection needle into an adrenal gland, the ablation needle device 100 including a metal injection needle 10 that includes a pointed tubular distal portion 11 and a tubular proximal portion 12 whose lumen communicates with a lumen of the distal portion 11 and has substantially the same diameter as the lumen of the distal portion 11; and a grip portion 20 attached to a proximal side of the injection needle 10, wherein the proximal portion 12 of the injection needle 10 is given flexibility (bendability) in a distal region 12A thereof by forming a helical slit 14 therein, and an outer surface of the proximal portion 12 is coated with coating resin 16; wherein the distal end of the distal portion 11 of the injection needle 10 is closed, and a plurality of fine holes 15 communicating with the lumen of the distal portion 11 are formed in an outer surface of the distal portion 11 including the closed part 13; wherein the grip portion 20 has an injection port 25 for supplying a physiological saline solution into the lumen of the injection needle 10; and wherein the grip portion 20 is provided with an energization connector 35 to be connected to a high-frequency power supply device so that a high-frequency current is supplied to the distal portion 11 of the injection needle 10, and to a thermocouple connector 45 connected to a temperature sensor (a thermocouple 40) provided in the distal portion 11 of the injection needle 10.

The ablation needle device 100 includes the injection needle 10 and the grip portion 20. The injection needle 10 includes the distal portion 11 and the proximal portion 12.

The length of the injection needle 10 is, for example, 400 to 2200 mm, preferably 600 to 1000 mm.

The outside diameter of the injection needle 10 (the distal portion 11 and the proximal portion 12) is, for example, 0.55 to 3.0 mm, preferably 0.7 to 2.0 mm.

The inside diameter of the injection needle 10 (the distal portion 11 and the proximal portion 12) is, for example, 0.25 to 2.8 mm, preferably 0.6 to 1.9 mm.

In the present embodiment in which the distal end of the proximal portion 12 is inserted in a proximal-end opening of the distal portion 11, the inside diameter of the proximal portion 12 is slightly smaller than the inside diameter of the distal portion 11. However, the two inside diameters are almost (substantially) the same.

Figure 2:
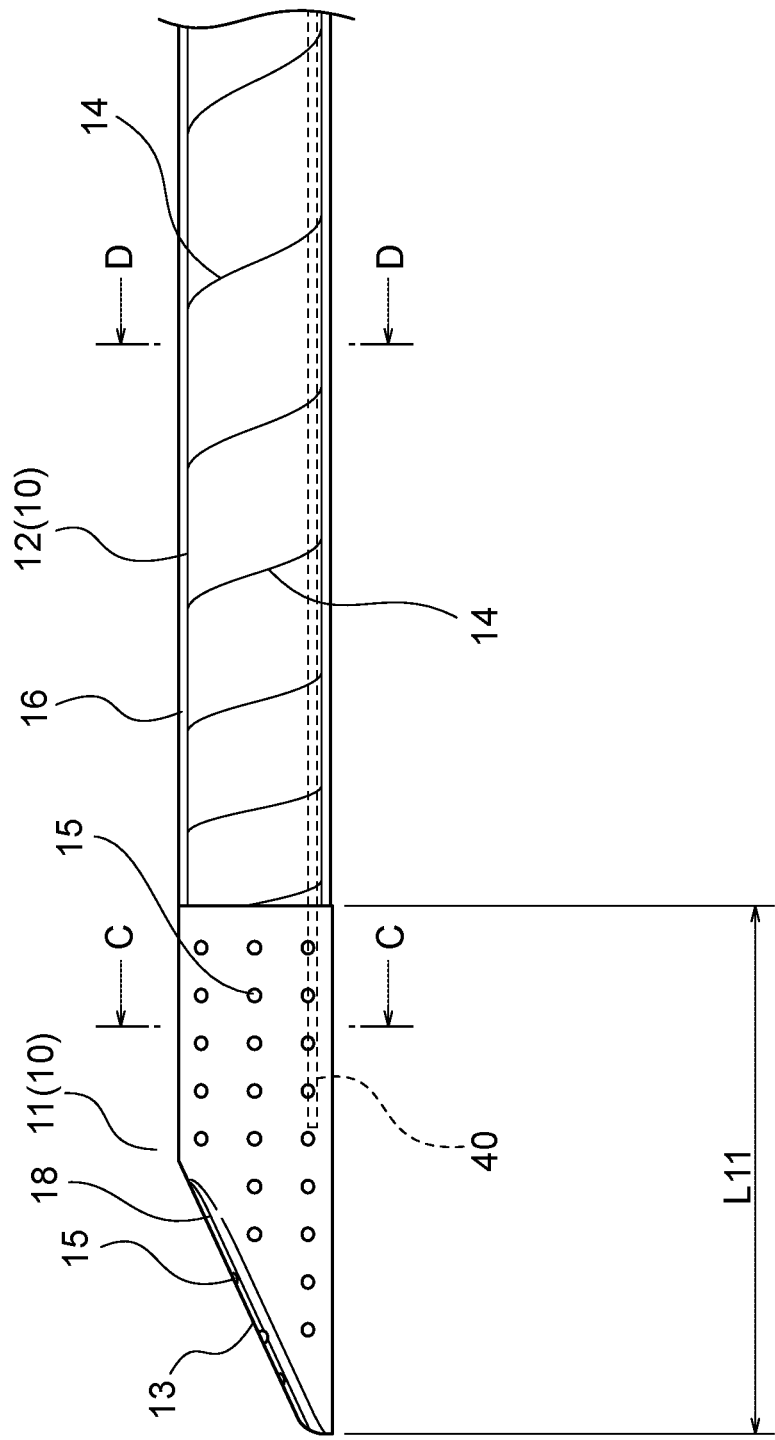
FIG. 2 is an enlarged partial side view (a detailed diagram of part A) of the ablation needle device illustrated in FIG. 1.
Figure 3:
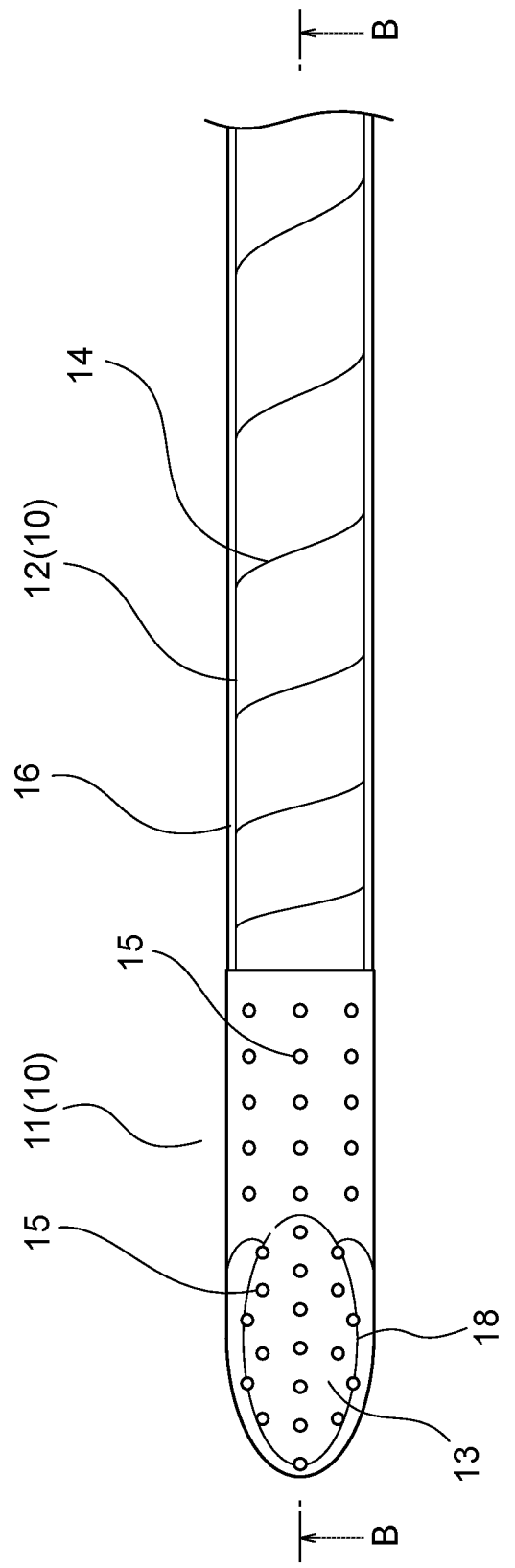
FIG. 3 is an enlarged partial plan view of the ablation needle device illustrated in FIG. 1.
Figure 4:
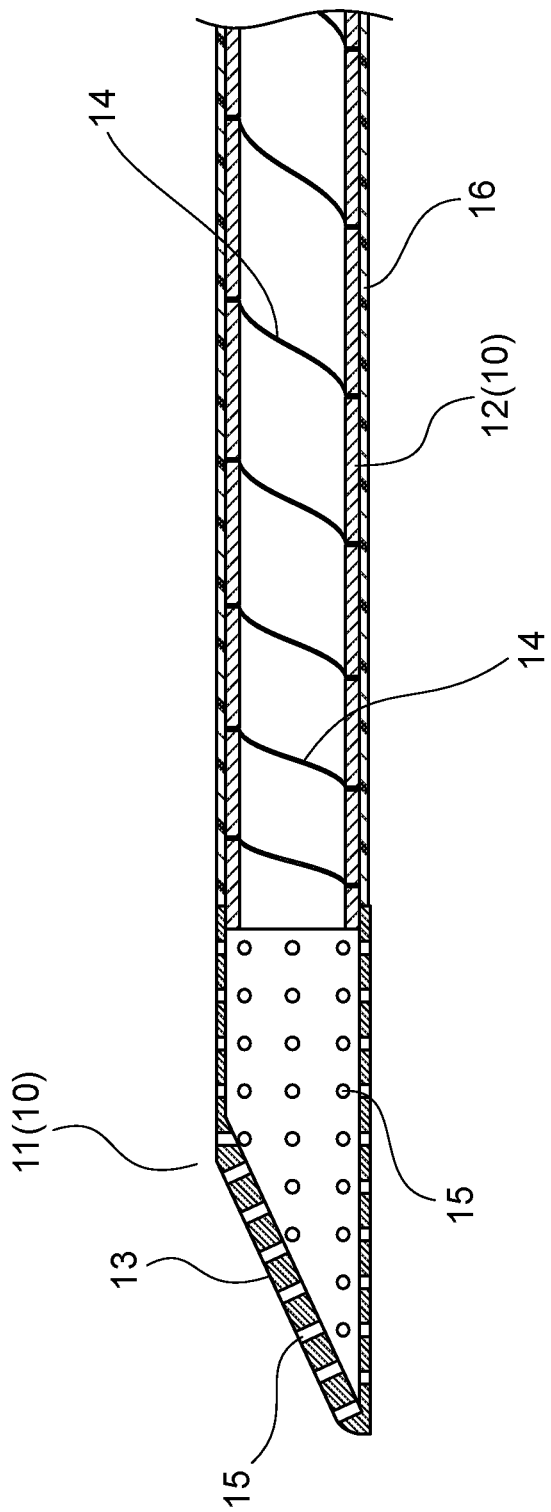
FIG. 4 is a longitudinal sectional view (taken along line B-B illustrated in FIG. 3) of the ablation needle device illustrated in FIG. 1.
Figure 5A:
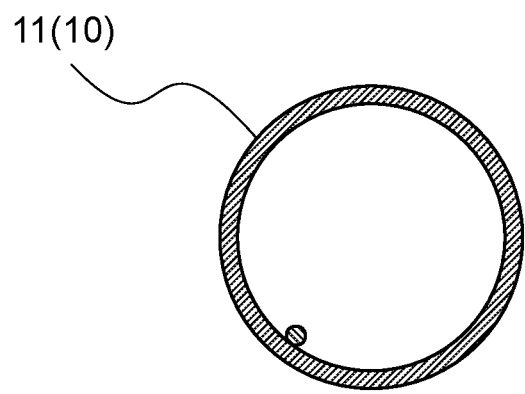
FIG. 5A is a lateral sectional view (taken along line C-C illustrated in FIG. 2) of the ablation needle device illustrated in FIG. 1.
Figure 5B:
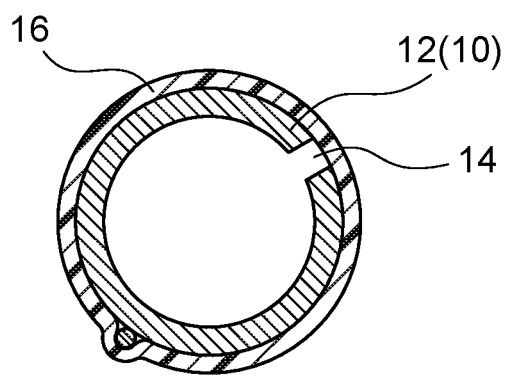
FIG. 5B is another lateral sectional view (taken along line D-D illustrated in FIG. 2) of the ablation needle device illustrated in FIG. 1.

As illustrated in FIGS. 2 to 4, the distal portion 11 of the injection needle 10 is made of a pointed metal tube, and the distal end thereof (a distal-end opening of a typical injection needle) is closed.

The plurality of fine holes 15 communicating with the lumen of the distal portion 11 are formed in the outer surface of the distal portion 11 including the closed part 13.

As illustrated in FIGS. 2 and 3, a blade 18 is formed at the outer edge of the closed part 13. The injection needle 10 can advance through the adrenal gland while tearing the tissue with the blade 18. Therefore, the distal portion 11 of the injection needle 10 can easily reach a target adenoma (a tumor to be treated).

Examples of the material for the distal portion 11 include stainless steel, NiTi, β-titanium, platinum-iridium, and the like.

The length (denoted by L11 in FIG. 2) of the distal portion 11 of the injection needle 10 is, for example, 1 to 6 mm, preferably 2.5 to 4.5 mm.

If the distal portion 11 is too short, the heat-generating area with respect to the target adenoma becomes too small. Accordingly, ablation nest(the region to be ablated) by such a distal portion becomes small, which may result in unsatisfactory effect of the treatment.

In contrast, if the distal portion 11 is too long, the followability of the injection needle with respect to the blood vessel may be deteriorated. Consequently, the injection needle may become unable to follow the venous blood vessel that meanders to the adrenal gland, being incapable of reaching the target adenoma.

The diameter of each of the fine holes 15 formed in the outer surface of the distal portion 11 is, for example, 0.01 to 0.25 mm, preferably 0.05 to 0.15 mm.

The density at which the fine holes 15 are formed is, for example, 4 to 100 holes/mm$^2$, preferably 9 to 30 holes/mm$^2$.

The proximal portion 12 of the injection needle 10 is a metal tube (a hypotube) in which the helical slit 14 is formed in the distal region 12A thereof.

Exemplary materials for the proximal portion 12 include the same metals as those for the distal portion 11.

The method of connecting the distal portion and the proximal portion of the injection needle is not specifically limited. In the present embodiment, the two are fixed to each other by inserting the distal end of the proximal portion 12 into the proximal-end opening of the distal portion 11.

The helical slit 14 formed in the distal region 12A of the proximal portion 12 is a through slit extending through the metal tube from the outer peripheral surface to the inner peripheral surface. The slit formed in the distal region of the proximal portion may be formed in such a manner as not to reach the inner peripheral surface.

Since the helical slit 14 is formed, the rigidity of the metal tube in that region is reduced to some extent, giving the metal tube flexibility (bendability). Hence, the injection needle 10 has excellent blood-vessel followability and can be easily made to follow the shape of the blood vessel reaching the adrenal gland.

In the distal region 12A (the region in which the slit 14 is formed) of the proximal portion 12, the pitch of the slit 14 is continuously reduced in a direction toward the distal end.

Thus, the rigidity of the distal region 12A of the proximal portion 12 can be continuously (smoothly) reduced in the direction toward the distal end. Accordingly, the needle device can exhibit especially high operability in the introduction of the injection needle 10 into the adrenal gland.

In the present invention, the slit formed in the distal region of the proximal portion may be at regular pitches over the entirety thereof.

The length of the proximal portion 12 of the injection needle 10 is, for example, 394 to 2199 mm, preferably 594 to 999 mm.

The length of the distal region 12A of the proximal portion 12, i.e., the region in which the slit 14 is formed, is, for example, 40 to 700 mm, preferably 80 to 600 mm.

If the region in which the slit 14 is formed is too short, the change in the hardness becomes too large. Consequently, the insertion characteristics may be deteriorated.

In contrast, if the region in which the slit 14 is formed is too long, the torque transmission may be reduced.

The method of forming the slit 14 in the distal region 12A is not specifically limited and may be laser machining, electric discharge machining, chemical etching, cutting, or the like.

The width of the slit 14 is, for example, 0.01 to 0.1 mm, preferably 0.02 to 0.04 mm.

The outer surface of the proximal portion 12 is coated with the insulating coating resin 16.

Hence, a high-frequency current flows between the distal portion 11 of the injection needle 10 and a counter-electrode plate (a high-frequency current is supplied to the distal portion 11 of the injection needle 10). Accordingly, the distal portion 11 serves as a distal-end electrode. Furthermore, since the slit 14 formed in the distal region 12A of the proximal portion 12 is closed by the coating resin 16, the injection needle 10 is assuredly made liquid-tight.

The film thickness of the coating resin 16 is, for example, 10 to 100 µm, preferably 20 to 40 µm.

The coating resin 16 is formed by shrinking a heat-shrinkable resin tube with the proximal portion 12 being inserted therein. An example of the heat-shrinkable resin tube forming the coating resin 16 may be polyether block amide copolymer resin (PEBAX, registered trademark).

When the ablation needle device 100 according to the present embodiment is included in a high-frequency ablation treatment system to be described below, a high-frequency ablation treatment of an adrenal tumor (a transvenous ablation treatment for primary aldosteronism) can be performed. Furthermore, since this ablation treatment is performed transvenously, a high-frequency ablation treatment of a tumor in the left adrenal gland, which has been difficult to perform in the known technique in which a high-frequency needle is stuck from the back, can be performed relatively easily.

Furthermore, since the helical slit 14 is formed in the distal region 12A of the proximal portion 12 of the injection needle 10, the rigidity in the distal region 12A is reduced to some extent, whereby the injection needle 10 can be made flexible. Therefore, the injection needle 10 can be made to follow the shape of the blood vessel reaching the adrenal gland, and the distal portion 11 of the injection needle 10 can be made to reach a tumor site in the adrenal gland, without damaging the vascular wall.

Furthermore, when a physiological saline solution is injected from the injection port 25, provided in the grip portion 20, during the high-frequency ablation treatment, the physiological saline solution can be ejected for irrigation from the plurality of fine holes 15 formed in the distal portion 11 of the injection needle 10. Thus, biological tissue or thrombi can be assuredly prevented from adhering to the surface of the distal portion 11 of the injection needle 10.

Second Embodiment

Figure 6:
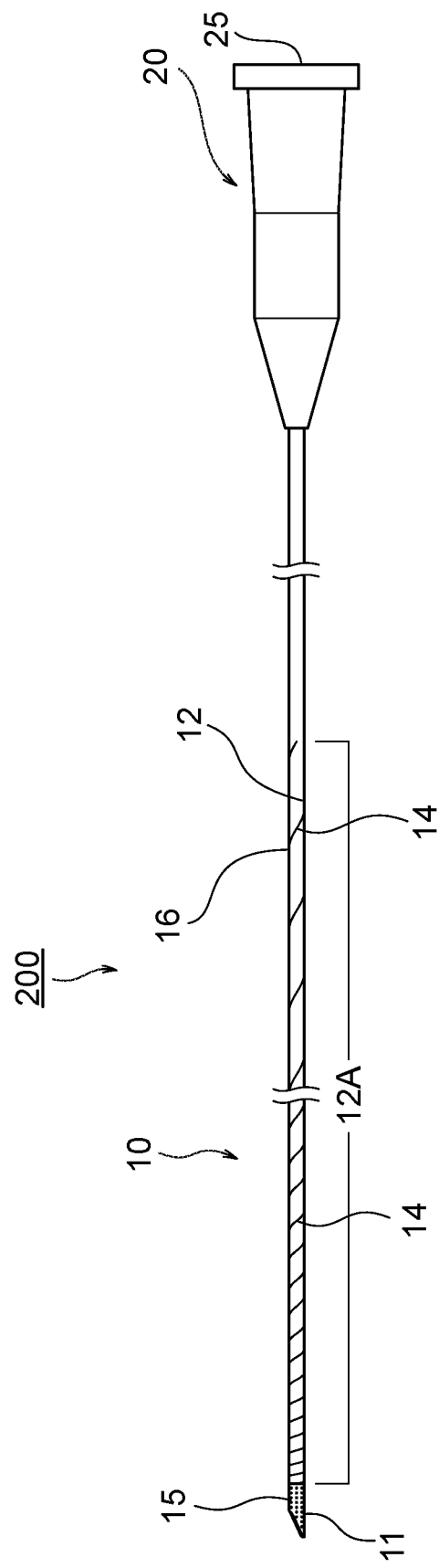
FIG. 6 is a side view of an ablation needle device according to another embodiment of the present invention.

An ablation needle device 200 according to the present embodiment illustrated in FIG. 6 is an ablation needle device intended for a chemical ablation treatment of an adrenal tumor in which ethanol is injected into the lumen of an injection needle 10 from an injection port 25 and is thus ejected for irrigation from a plurality of fine holes 15 formed in a distal portion 11 of the injection needle 10.

In FIG. 6, elements denoted by the same reference numerals as those used in FIG. 1 are the same as respective elements included in the ablation needle device 100 according to the first embodiment. The ablation needle device 200 according to the present embodiment is an ablation needle device intended for a chemical ablation treatment. Therefore, the grip portion 20 included in the ablation needle device 200 is provided with neither the energization connector nor the thermocouple connector.

When the ablation needle device 200 according to the present embodiment is included in a chemical ablation treatment system to be described below (when ethanol-supplying means is connected to the injection port 25), a chemical ablation treatment of an adrenal tumor (a transvenous ablation treatment) can be performed.

Furthermore, since the helical slit 14 is formed in the distal region 12A of the proximal portion 12 of the injection needle 10, the injection needle 10 can be made to follow the shape of the blood vessel reaching the adrenal gland. Consequently, the distal portion 11 of the injection needle 10 can be made to reach a tumor site in the adrenal gland, without damaging the vascular wall.

<High-Frequency Ablation Treatment System>

Figure 7:
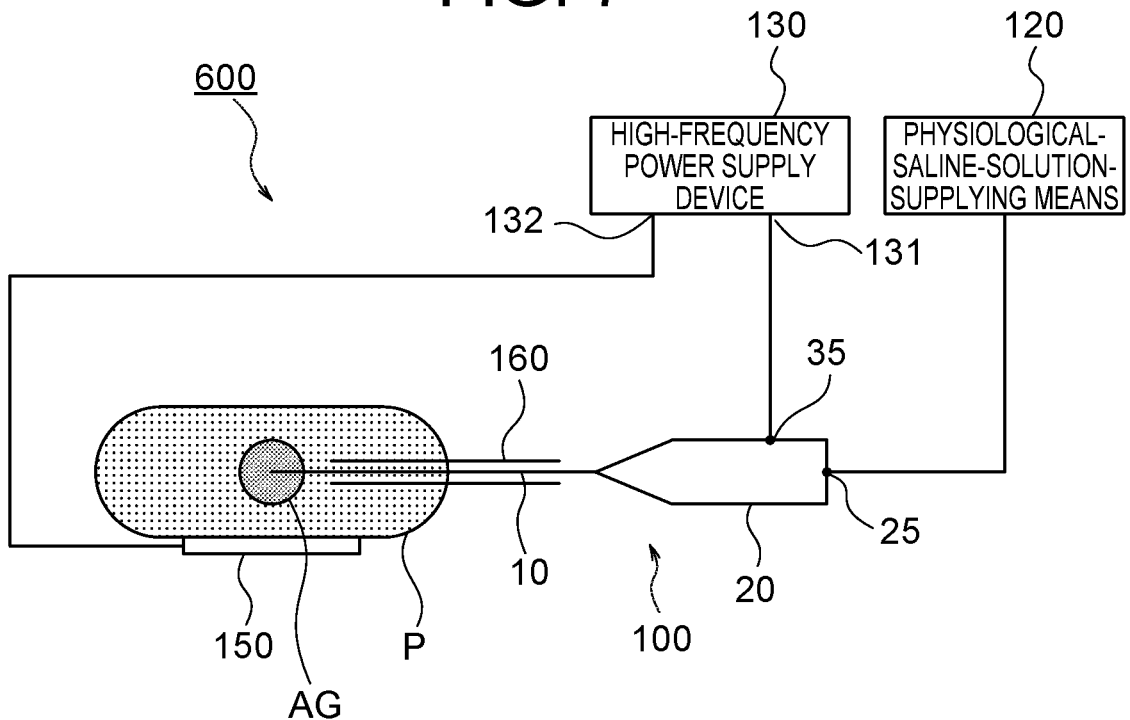
FIG. 7 is a schematic diagram illustrating a configuration of a high-frequency ablation treatment system according to the present invention.

A high-frequency ablation treatment system 600 according to the present embodiment illustrated in FIG. 7 includes the ablation needle device 100 according to the first embodiment, a high-frequency power supply device 130 connected to the energization connector 35 of the ablation needle device 100, a counter-electrode plate (patient plate) 150 connected to the high-frequency power supply device 130, physiological-saline-solution-supplying means 120 connected to the injection port 25 of the ablation needle device 100, and a guiding catheter 160 for guiding the distal portion of the injection needle 10 to an adrenal gland AG of a patient P.

As illustrated in FIG. 7, the energization connector 35 of the ablation needle device 100 is connected to a needle-device-connecting connector 131 included in the high-frequency power supply device 130. A counter-electrode-plate-connecting connector 132 included in the high-frequency power supply device 130 is connected to the counter-electrode plate 150.

This enables a high-frequency current to flow between the distal portion of the injection needle 10 of the ablation needle device 100 and the counter-electrode plate 150 (a high-frequency ablation treatment of an adrenal tumor can be performed).

The physiological-saline-solution-supplying means 120 is connected to the injection port 25 of the grip portion 20 of the ablation needle device 100.

Hence, during a high-frequency ablation treatment, a physiological saline solution can be injected from the physiological-saline-solution-supplying means 120 into the lumen of the injection needle 10 through the injection port 25, and the physiological saline solution can be ejected for irrigation from the plurality of fine holes formed in the distal portion of the injection needle 10.

The guiding catheter 160 included in the high-frequency ablation treatment system 600 is inserted in advance such that the distal end thereof is positioned in (near) the adrenal gland, in order to guide the distal portion of the injection needle 10 of the ablation needle device 100 to the adrenal gland AG of the patient P.

The shape of the guiding catheter 160 schematically illustrated in FIG. 7 depends on whether it is intended for the right adrenal gland or the left adrenal gland, because the blood vessels reaching the respective adrenal glands have different shapes.

Figure 9A:
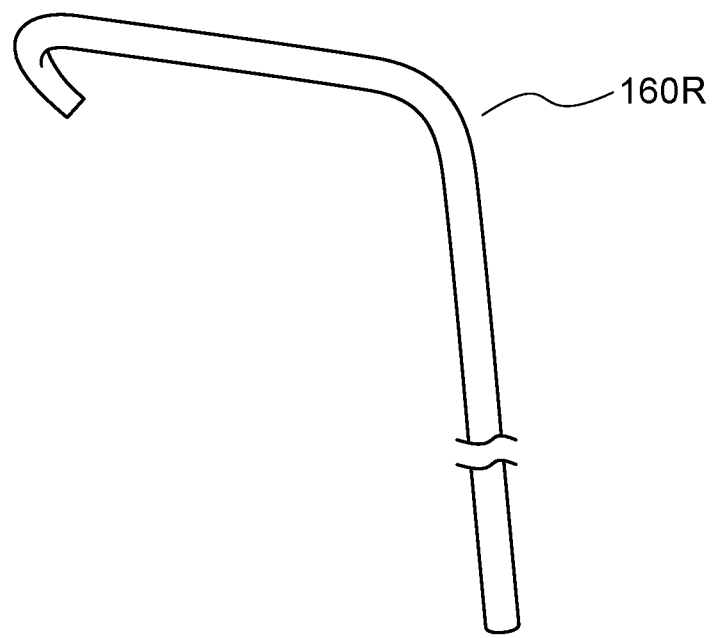
FIG. 9A is a diagram illustrating the shape of a guiding catheter for the right adrenal gland that is included in the high-frequency ablation treatment system or the chemical ablation treatment system according to the present invention.
Figure 9B:
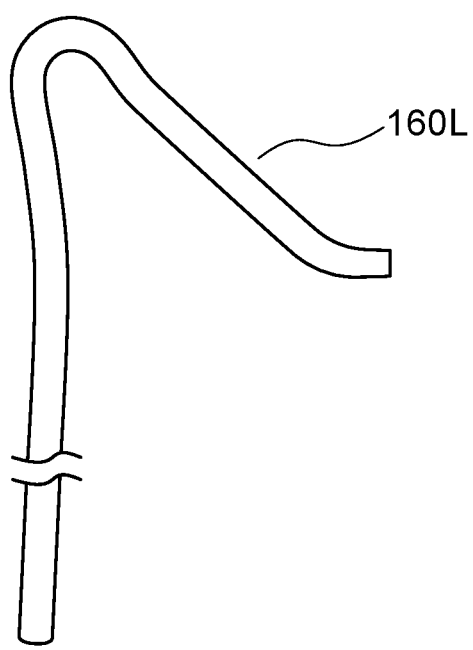
FIG. 9B is a diagram illustrating the shape of a guiding catheter for the left adrenal gland that is included in the high-frequency ablation treatment system or the chemical ablation treatment system according to the present invention.

FIG. 9A illustrates the shape of a distal portion of a guiding catheter 160R for the right adrenal gland. FIG. 9B illustrates the shape of a distal portion of a guiding catheter 160L for the left adrenal gland.

The guiding catheters 160R and 160L illustrated in FIGS. 9A and 9B each have a plurality of curved parts.

When the distal region of the injection needle 10 is projecting from the distal-end opening of the guiding catheter 160R or 160L, the proximal end of the region of the injection needle 10 where the slit 14 is formed is desirably positioned further on the proximal side with respect to the proximal end of one of the curved parts of the guiding catheter that is at the most proximal side. Thus, the needle device can exhibit especially high operability.

Figure 10A:
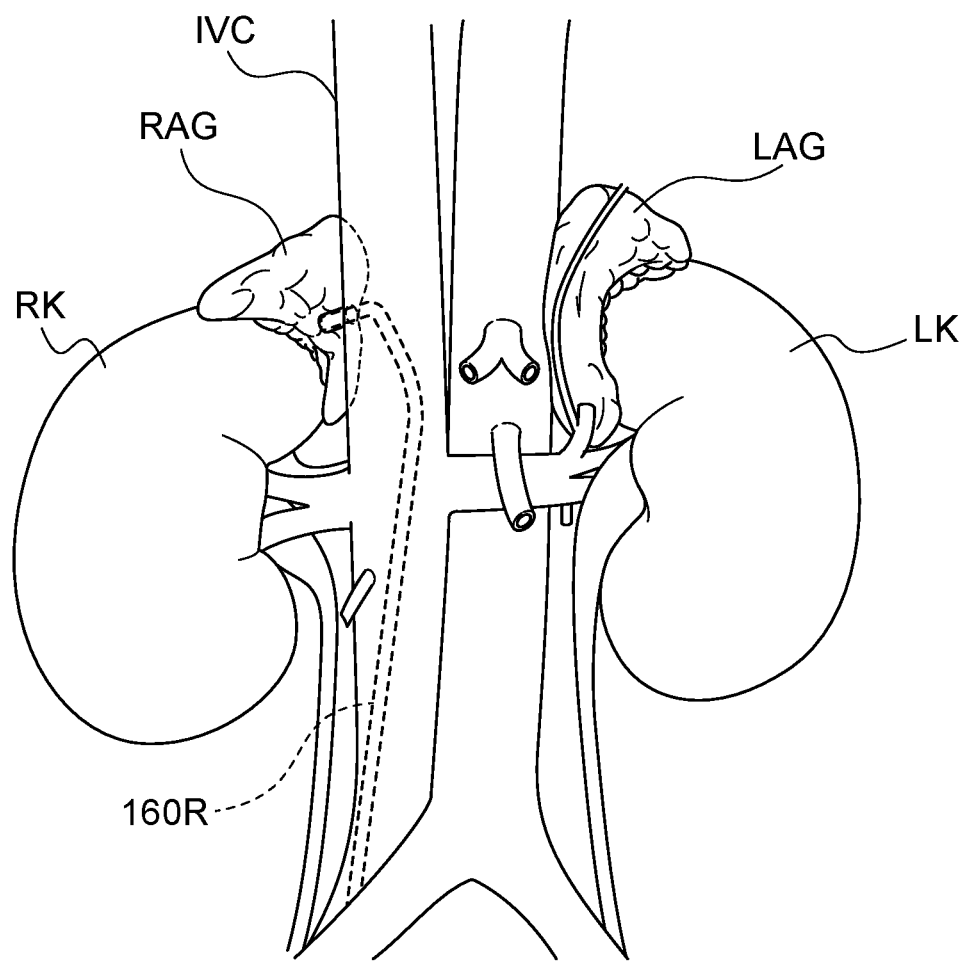
FIG. 10A is a diagram illustrating a state where the distal end of the guiding catheter illustrated in FIG. 9A has reached the right adrenal gland.

The guiding catheter 160R for the right adrenal gland that is illustrated in FIG. 9A is inserted such that, as illustrated in FIG. 10A, the distal end thereof is positioned at (near) a right adrenal gland RAG through an inferior vena cava IVC and the right adrenal vein. The guiding catheter 160L for the left adrenal gland that is illustrated in FIG. 9B is inserted such that, as illustrated in FIG. 10B, the distal end thereof is positioned at (near) a left adrenal gland LAG through the inferior vena cava IVC, a left renal vein LRV, and the left adrenal vein.

Figure 10B:
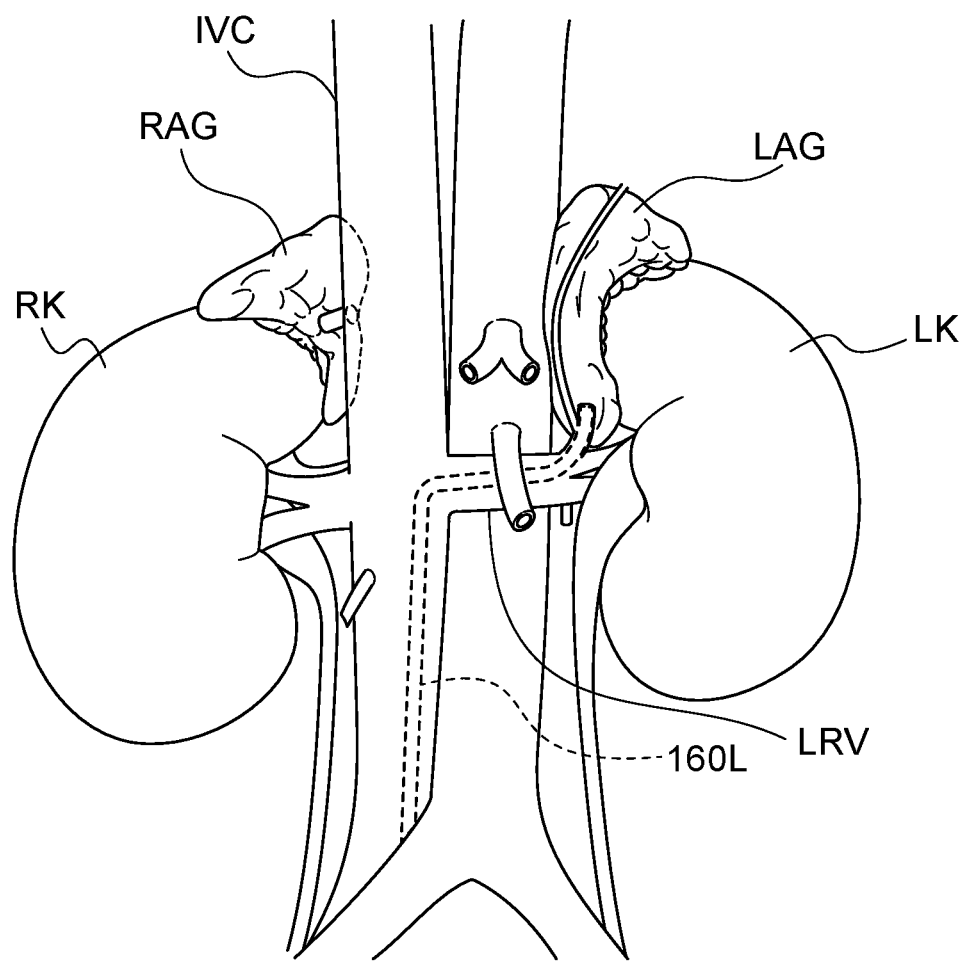
FIG. 10B is a diagram illustrating a state where the distal end of the guiding catheter illustrated in FIG. 9B has reached the left adrenal gland.

In FIGS. 10A and 10B, RK denotes the right kidney, and LK denotes the left kidney.

The outside diameter of the guiding catheter 160 (160R, 160L) is, for example, 1.0 to 4.0 mm, preferably 1.5 to 2.7 mm.

The inside diameter of the guiding catheter 160 is, for example, 0.6 to 3.1 mm, preferably 0.75 to 2.1 mm.

The length of the guiding catheter 160 is, for example, 350 to 2100 mm, preferably 550 to 950 mm.

The guiding catheter 160 (160R, 160L) may be a catheter used for sampling blood from the adrenal vein (adrenal venous sampling).

With the high-frequency ablation treatment system 600 according to the present embodiment, a high-frequency ablation treatment (a low-invasive transvenous ablation treatment) of an adrenal tumor can be performed by causing a high-frequency current to flow between the distal portion of the injection needle 10 of the ablation needle device 100 and the counter-electrode plate 150.

Furthermore, during the high-frequency ablation treatment, when the physiological saline solution supplied from the physiological-saline-solution-supplying means 120 is ejected for irrigation from the plurality of fine holes formed in the distal portion of the injection needle 10 of the ablation needle device 100, biological tissue or thrombi can be assuredly prevented from adhering to the surface of the distal portion of the injection needle 10.

<Chemical Ablation Treatment System>

Figure 8:
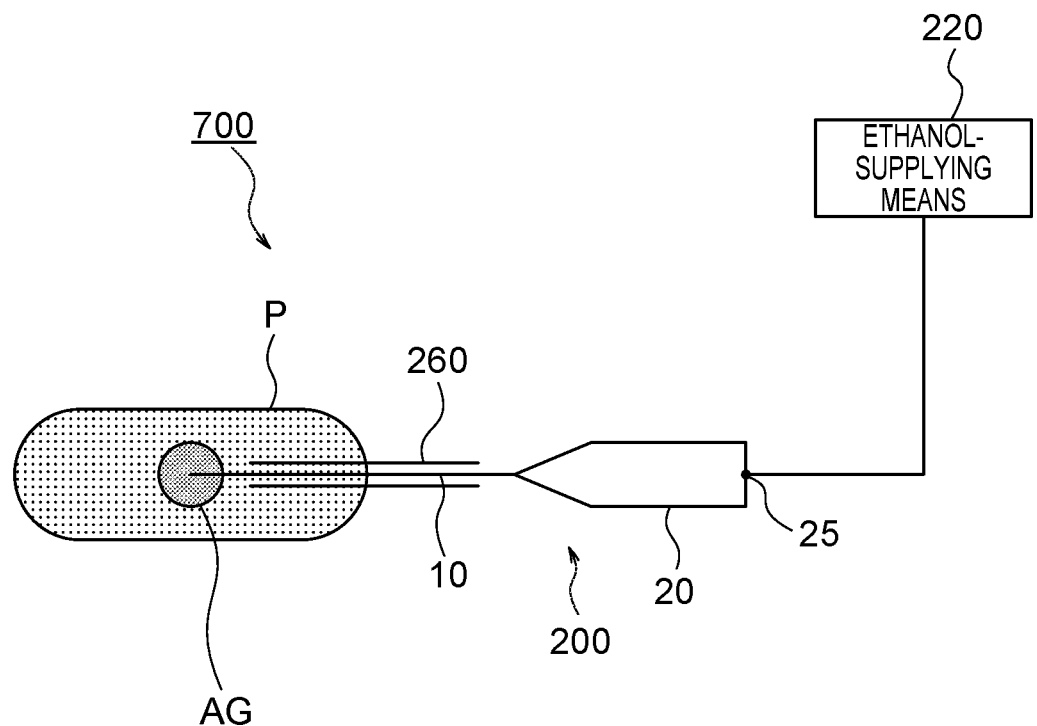
FIG. 8 is a schematic diagram illustrating a configuration of a chemical ablation treatment system according to the present invention.

A chemical ablation treatment system 700 according to an embodiment illustrated in FIG. 8 includes the ablation needle device 200 according to the second embodiment, ethanol-supplying means 220 connected to the injection port 25 of the ablation needle device 200, and a guiding catheter 260 for guiding the distal portion of the injection needle 10 to the adrenal gland AG of the patient P.

The ethanol-supplying means 220 is connected to the injection port 25 of the grip portion 20 of the ablation needle device 200.

Hence, ethanol can be injected from the ethanol-supplying means 220 into the lumen of the injection needle 10 through the injection port 25, and a chemical ablation treatment of an adrenal tumor can be performed while the ethanol is ejected from the plurality of fine holes formed in the distal portion of the injection needle 10.

The guiding catheter 260 included in the chemical ablation treatment system 700 has the same configuration as the guiding catheter 160 (160R, 160L) included in the high-frequency ablation treatment system 600 illustrated in FIGS. 7, 9 (9A, 9B), and 10 (10A, 10B).

With the chemical ablation treatment system 700 according to the present embodiment, a chemical ablation treatment (a low-invasive transvenous ablation treatment) of an adrenal tumor can be performed by ejecting the ethanol supplied from the ethanol-supplying means 220 from the plurality of fine holes formed in the distal portion of the injection needle 10 of the ablation needle device 100 and by bringing the ethanol into contact with the tumor tissue.

REFERENCE SIGNS LIST 100 ablation needle device
10 injection needle
11 distal portion
12 proximal portion
12A distal region of proximal portion
13 closed part
14 slit
15 fine hole
16 coating resin
18 blade
20 grip portion
25 injection port
35 energization connector
40 temperature sensor (thermocouple)
45 thermocouple connector
120 physiological-saline-solution-supplying means
130 high-frequency power supply device
150 counter-electrode plate
160 (160R, 160L) guiding catheter
200 ablation needle device
220 ethanol-supplying means
260 guiding catheter
600 high-frequency ablation treatment system
700 chemical ablation treatment system

The invention claimed is:

1. An ablation needle device intended for an ablation treatment of an adrenal tumor with transvenous introduction of an injection needle into an adrenal gland, the ablation needle device comprising:
   a metal injection needle including a pointed tubular distal portion and a tubular proximal portion whose lumen communicates with a lumen of the distal portion and has substantially the same diameter as the lumen of the distal portion; and a grip portion attached to a proximal side of the injection needle,
   wherein the proximal portion of the injection needle is given flexibility by forming a helical slit at least in a distal region of the proximal portion, and an outer surface of the proximal portion is coated with resin,
   wherein a distal end of the distal portion of the injection needle is closed, and a plurality of fine holes communicating with the lumen of the distal portion are formed in an outer surface of the distal portion including the closed part,
   wherein the outer surface of the distal portion is not coated with resin and exposes a metal surface,
   wherein the grip portion has a liquid-injection port for supplying liquid into the lumen of the injection needle,
   wherein in order to perform high-frequency ablation treatment by supplying the high-frequency current to the distal portion of the injection needle to heat adrenal tumor tissue around the distal portion of the injection needle, the grip portion has an energization connector for supplying the high-frequency current to the distal portion of the injection needle, and thereby the distal portion functions as a distal electrode, and
   wherein the injection port is an injection port for a physiological saline solution, and irrigation with the physiological saline solution through the plurality of fine holes is performed by injecting the physiological saline solution into the lumen of the injection needle from the injection port.

2. The ablation needle device according to claim 1, wherein a pitch of the slit formed in the proximal portion of the injection needle is continuously or intermittently reduced in a direction toward the distal end.

3. ablation needle device according to claim 1,
wherein the distal portion of the injection needle has a length of 1 to 6 mm, and the region of the proximal portion of the injection needle where the slit is formed has a length of 40 to 700 mm, and
wherein the injection needle has an inside diameter of 0.25 to 2.8 mm, and the fine holes each have a diameter of 0.01 to 0.25 mm.

4. The ablation needle device according to claim 1, wherein the grip portion has a thermocouple connector for measuring a temperature of the distal portion of the injection needle.

5. A high-frequency ablation treatment system for an adrenal tumor, the system comprising:
the ablation needle device according to claim 1;
a high-frequency power supply device connected to the energization connector;
a counter-electrode plate connected to the high-frequency power supply device;
physiological-saline-solution-supplying means connected to the injection port; and
a guiding catheter for guiding the distal portion of the injection needle to the adrenal gland.

* * * * *